United States Patent [19]

Sebastian et al.

[11] Patent Number: 5,122,111
[45] Date of Patent: Jun. 16, 1992

[54] LUMBAR SUPPORT HAVING REPOSITIONABLE PAD-ACCOMMODATING POUCHES

[75] Inventors: Peter R. Sebastian, Salisbury, Md.; Thomas V. Sebastian, Reading, Pa.

[73] Assignee: Safeguard Industrial Corporation, Leesport, Pa.

[21] Appl. No.: 727,221

[22] Filed: Jul. 3, 1991

Related U.S. Application Data

[63] Continuation-in-part of Ser. No. 678,938, Apr. 3, 1991, abandoned.

[51] Int. Cl.$^5$ ............................................. A61F 5/02
[52] U.S. Cl. ...................... 602/19; 128/108.1; 128/109.1; 128/112.1
[58] Field of Search .................. 128/78, 95.1, 96.1, 128/99.1, 100.1, 101.1, 106.1, 107.1, 108.1, 109.1, 111.1, 112.1, 116.11; 272/119, 139, 143; 2/311, 312, 319

[56] References Cited

U.S. PATENT DOCUMENTS

| 3,265,064 | 8/1966 | Gruber . |
| 3,554,190 | 1/1971 | Kaplan . |
| 4,159,020 | 6/1979 | von Soiron et al. . |
| 4,178,923 | 12/1979 | Curlee . |
| 4,269,179 | 5/1981 | Burton et al. . |
| 4,586,506 | 5/1986 | Nangle . |
| 4,641,642 | 2/1987 | Williams, Jr. . |
| 4,907,576 | 3/1990 | Curlee . |
| 4,960,112 | 10/1990 | Anderegg . |
| 4,993,409 | 2/1991 | Grim ........................ 128/78 |
| 5,007,412 | 4/1991 | DeWall . |
| 5,040,524 | 8/1991 | Votel et al. . |

FOREIGN PATENT DOCUMENTS

| 578241 | 5/1933 | Fed. Rep. of Germany . |
| 2569344 | 2/1986 | France ........................ 128/80 C |

Primary Examiner—Richard J. Apley
Assistant Examiner—Linda C. M. Dvorak
Attorney, Agent, or Firm—Wenderoth, Lind & Ponack

[57] ABSTRACT

A therapeutic appliance is securable in an operative orientation around the abdominal region of the body for therapeutically treating the lumbar area and upper portion of the sacrum. The appliance includes an external shell securable about the abdominal region of the body and pouches repositionably attached to the shell for accommodating various types of therapeutic pads. Each of the pouches may be moved or pivoted between a position at which the pad accommodated therein will overlie the lumbodorsal fascia and quadratus lumborum muscles and a second position at which the pad will overlie the erector spinae muscles. In addition, a band-like elastic member is secured to the shell in a manner in which the elastic member may exert tension over the pouches. Opposite ends of the elastic member can be secured at various locations along opposite ends of the external shell so that the tension of the elastic member can be varied. Further, releasable suspender straps are provided to maximize comfort and to minimize the likelihood of user injury caused by snagging of the suspender straps.

33 Claims, 2 Drawing Sheets 5,122,111

LUMBAR SUPPORT HAVING REPOSITIONABLE PAD-ACCOMMODATING POUCHES

CROSS REFERENCE TO RELATED APPLICATION

This application is a Continuation-In-Part application of application Ser. No. 07/678,938, filed Apr. 3, 1991, now abandoned.

BACKGROUND OF THE INVENTION

The present invention relates to a therapeutic appliance for application to the lumbar area and upper portion of the sacrum.

Low back pain commonly arises in individuals due to alterations in the biomechanics of the lumbosacral spine and its supporting muscular and ligamentous structures. Therapeutic appliances can be useful, both in the treatment and prevention of back pain in individuals, when the primary mechanism involved in the generation of pain is due to muscular strain, spasm, or fatigue. The resulting pain can be produced within the muscles themselves or from the secondary effects from loss of adequate and balanced support to the osseous and ligamentous structures of the lower back, whose movements they regulate.

Known supports have been designed in an attempt to limit fatigue and undue strain in the above-mentioned structures and to aid in the restoration of both normal and balance muscle tone. While such aims are rarely achieved by the application of known therapeutic appliances alone, such appliances are often helpful in the prevention and treatment of various lower back conditions.

However, even these appliances are apt to exhibit one or more significant disadvantages. For example, some supports contain rigid elements or narrow elastic bands which will often dig into the skin or produce irritation over bony protuberances. This will often lead to noncompliance by the user. Some of the currently available therapeutic appliances designed for application to the lower back fail to provide support over the entire lumbar area, either having too narrow a width or inadequate supporting elements at the top and/or bottom of the device. Other devices are limited in their usefulness by applying support only over the most central areas of the spine.

Further, while rigid immobilization is desirable in certain types of spine injury, excessive limitation of spine movement for the muscular conditions previously described can be unwanted and create weakness through disuse of the supporting musculature.

Further, in known lumbar support appliances utilizing shoulder suspenders, the suspender straps are sewn to the body of the appliance. Such appliances suffer a drawback in that the suspenders can potentially be snagged by a stationary or non-stationary piece of industrial equipment, thus entangling the user with the equipment. Such entanglement could result in serious injury to the user.

SUMMARY OF THE INVENTION

An object of the present invention is to provide a therapeutic appliance which is comfortable to wear, which adequately covers the lumbar region and which can provide optimum support and/or therapeutic treatment for the lower back.

Another object of the present invention is to provide a therapeutic appliance which can provide support for the lower back without limiting the range of motion and without inhibiting necessary voluntary muscle activity.

Yet another object of the present invention is to provide a shoulder suspender arrangement, to be used in combination with the therapeutic appliance, which reduces the risk of injury to the user of the appliance resulting from snagging of the suspender straps by a stationary or non-stationary piece of equipment.

To achieve these objects, the therapeutic appliance of the present invention comprises an external shell securable about the abdominal region of the body, and pouches repositionably attached to the shell for accommodating various types of therapeutic pads such as a foam pad, an inflatable air bladder, a heat source or a cold source. Each of the pouches may be moved or pivoted between a position at which the pad accommodated therein will overlie the lumbodorsal fascia and quadratus lumborum muscles and a second position at which the pad will overlie the erector spinae muscles. Further, the central section of the shell, at which the pad-accommodating pouches are located, has such a width that the appliance will cover the lumbar area and the upper portion of the sacrum.

In addition, a band-like elastic member is secured to the shell in a state of tension over the pouches whereby the pads accommodated in the pouches will be urged into engagement with the lower back. Opposite ends of the elastic member can be secured at various locations along opposite ends of the external shell whereby the tension of the elastic member can be varied to adjust the tension of the appliance and/or the force at which the pads are urged into engagement with the lower back.

In addition, break away shoulder suspenders are provided. The shoulder suspenders are formed of an elastic woven material and are secured to the external shell of the therapeutic appliance by hook and loop closures. By the provision of the hook and loop closures, the suspender will tend to break away from the external shell of the therapeutic appliance in the event that the shoulder suspenders are somehow snagged by a piece of equipment. Further, the provision of the shoulder suspenders permits the user of the appliance to loosen the fastener of the appliance to allow evaporation of moisture and dissipation of heat. Further, the shoulder suspenders could be detached from the therapeutic appliance altogether if desired.

BRIEF DESCRIPTION OF THE DRAWINGS

These and other objects, features and advantages of the present invention will become apparent to those ordinary skill in the art by referring to the detailed description thereof below in conjunction with the accompanying drawings, in which.

DETAILED DESCRIPTION OF THE PREFERRED EMBODIMENT

Figure 3:
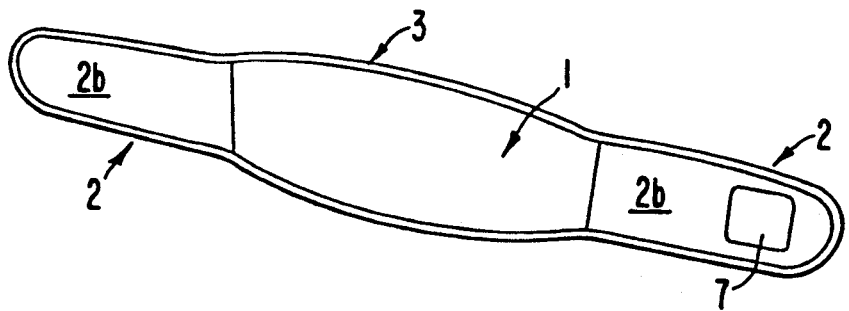
FIG. 3 is a perspective view of the shell of the appliance of FIG. 1 as seen from the other side thereof.

The therapeutic appliance of the present invention has an external shell including a central region generally designated by reference numeral 1 and opposite ends designated by reference numeral 2. The external shell, including the central region 1 and opposite ends 2, is fabricated from material having a degree of elasticity and the shape best shown in FIG. 3. Such material is preferably a known knit material. At the outer side of the shell shown in FIG. 1, such knit material is covered at the opposite ends 2 with pieces of material 2a to be described in more detail below. On the opposite side of the shell, as shown in FIG. 3, the ends of the knit material are covered by pieces of plush foam 2b. The pieces of material 2a, the pieces of plush foam 2b and the ends of the knit material interposed therebetween are sewn together so as to constitute the external shell. This may be accomplished by stitching a bias binding 3 at the periphery of the external shell.

A plurality of stiffening members 4a–4f are also secured to the external shell. The stiffening members 4a–4f preferably include a semi-rigid strip of KYDEC material enclosed within a CAMBRELLE sleeve. The sleeves of the stiffening members 4a–4f can be secured to the external shell by means of stitching. In this respect, the bias binding 3 is also used to stitch the ends of the sleeves of the stiffening members 4a–4f to the external shell.

Figure 1:
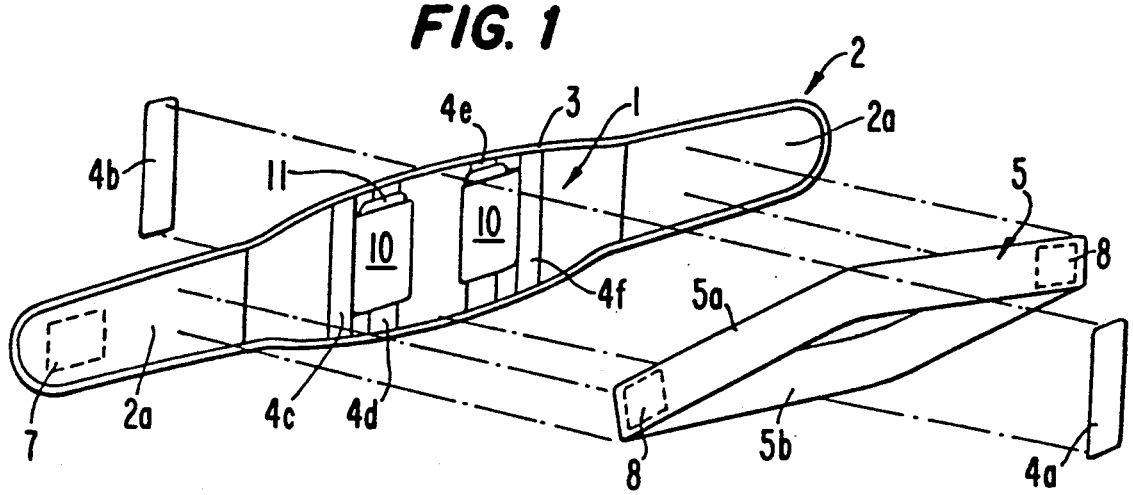
FIG. 1 is an exploded view of an embodiment of a therapeutic appliance according to the present invention.
Figure 2:
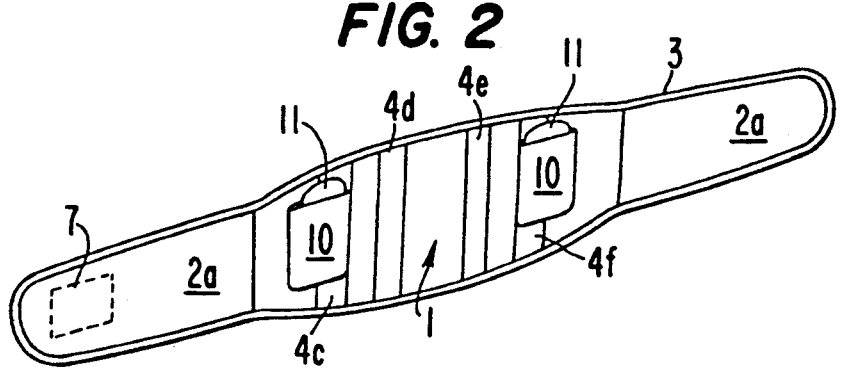
FIG. 2 is a perspective view of the therapeutic appliance shown in FIG. 1 but with the pouches shown in a different position and various elements omitted for the sake of clarity.
Figure 4A:
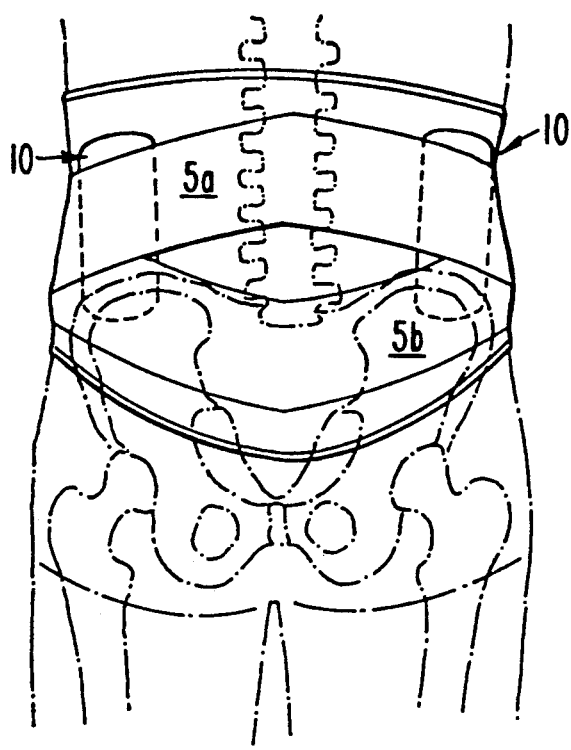
FIGS. 4(a) and 4(b) are schematic diagrams showing the therapeutic appliance of FIG. 1 secured around the abdominal region of the body with the pads assuming positions corresponding to those illustrated in FIG. 2 and FIG. 1, respectively.
Figure 4B:
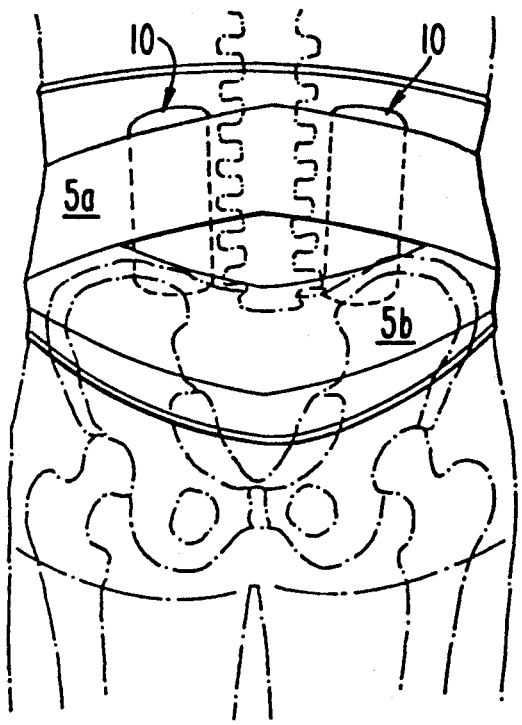

As best seen in FIGS. 1 and 2, pouches 10, which can be fabricated of CAMBRELLE, are pivotably attached to the external shell at one side thereof, preferably the outer side facing away from the user of the appliance. Each of the pouches 10 is located at the central region 1 of the shell to a respective side of the midpoint between the opposite ends 2. And, the pouches 10 are attached at only one side thereof to the belt (the sides adjacent stiffening members 4c, 4f, respectively, in FIG. 1). Thus, each pouch can be pivotable about one side thereof between a first position shown in FIG. 2 in which the pouch is disposed at a location between the longitudinal midpoint of the shell and a respective one of the ends of the shell and a second position shown in FIG. 1 at which the pouch is disposed at a location closer to the midpoint from the first position. Turning to FIGS. 4(a) and 4(b), the first position as shown in FIG. 4(a) is one at which the pouch 10 will overlie the lumbodorsal fascia and quadratus lumborum muscles when the shell is secured around the abdominal region of the body. As shown in FIG. 4(b) the second position is one at which the pouches will overlie the erector spinae muscles when the shell is secured around the abdominal region of the body.

As is also apparent from FIG. 4(a), the central region 1 of the external shell has a width that is sufficient to enable the appliance to cover the lumbar area and the upper portion of the sacrum. And, the lower edge of the appliance is contoured to limit bony bridging from the iliac crest.

The pouches 10 may take the form of a sleeve open at the top thereof so as to accommodate a therapeutic pad 11 according to the present invention. The therapeutic pad 11 is of a type necessary to impart a desired therapeutic treatment to the lower back. For instance, the therapeutic pad 11 may be a foam pad for providing support to the lower back, an inflatable air bladder for providing support to the lower back, a heat-retaining pad known per se for radiating therapeutic amounts of heat to the lower back, or a known type of cold-pack for applying therapeutic amounts of cold to the lower back. Thus, the therapeutic appliance of the present invention may be provided as a kit including a plurality of pads of any of the above-mentioned types which may be suitably selected and inserted into the pouches 10 to carry out a desired therapeutic treatment.

It should thus be quite apparent that because the pouches can be positioned medially over the erector spinae muscles or laterally over the lumbodorsal fascia and quadratus lumborum muscles, the therapeutic pads 11 accommodated in the pouches 10 can likewise be positioned medially over the erector spinae muscles or laterally over the lumbodorsal fascia and quadratus lumborum muscles. In addition, and again depending upon the particular case at hand, the pouches 10 can be fill with a therapeutic pad 11 on one or both sides of the appliance or can even remain empty.

Referring once again to FIG. 1, a band-like elastic member 5 is attached at a central portion thereof to the external shell between the stiffening members 4a, 4b. Although the stiffening members 4a, 4b are shown as being attached to opposite sides of the appliance with the central portion of the elastic member 5 interposed therebetween, in practice, the stiffening member 4b may be disposed on the same side of the belt as the stiffening member 4a but with the central portion of the elastic member 5 still interposed between members 4a, 4b.

In the embodiment shown in the figures, the band-like elastic member 5 is in the form of a loop of knitted elastic material having upper and lower elastic band sections 5a, 5b which will be described in more detail below. The external shell and the elastic member include fasteners at the ends thereof for detachably securing the ends of the elastic member 5 to various locations along the ends 2 of the external shell. For example, the fasteners can be well-known hook and loop types of fasteners, such as VELCRO fasteners, by forming the pieces of material 2a as loop-type fastener members and by providing the ends of the band-like elastic member 5 with hook-type fastener members 8.

With the ends of the band-like elastic member 5 secured to the ends 2 of the external shell, the elastic member 5 extends over the central region 1 of the external shell in a state of tension over the pouches 10 whereby any pads 11 accommodated in the pouches 10 will be urged into engagement with the lower back. Because the opposite ends of the elastic member 5 can be secured to various locations along opposite ends 2 of the external shell, the tension of the elastic member 5 can be varied to adjust the force at which the pads 11 are urged into engagement with the lower back or simply to adjust the tension of the appliance around the abdominal region.

Referring once again to FIGS. 4(a) and 4(b), the upper elastic band 5a extends across the central region 1 of the external shell at such a location as to be aligned transversely across the lumbar area when the appliance is secured around the abdominal region. The lower elastic band 5b is inclined upwardly from the central portion of member 5 toward the upwardly elastic band 5a.

In addition, it should be noted that closure members are provided at the opposite ends 2 of the external shell for detachably securing the ends together so as to allow the appliance to be detachably secured around the abdominal region of the body in the position schematically illustrated in FIGS. 4(a) and 4(b). If, the pieces of material 2a are in the form of loop-type fastening members as described above, a hook-type fastening member 7 may be secured at one end of the shell at the side thereof opposite to the side at which the loop-type fastening members are exposed. In this way, the loop-type fastening members 2a, constituting a means for fastening the ends of the elastic member 5 to the ends of the external shell, will also constitute closure means with the hook-type fastening member 7 for allowing the appliance to be detachably secured around the abdominal region of the body.

From the above-described description of the preferred embodiment, it should be clear that the present invention exhibits the following features and advantages, among others:

(1) the central region of the appliance has a width which is sufficient to cover the lumbar area and upper portion of the sacrum;

(2) the lower edge of the shell is contoured to limit bony bridging from the iliac crest;

(3) an upper tension-exerting elastic band is aligned transversely across the lumbar area while the lower elastic band is angulated upwardly and laterally;

(4) pouches are provided on both sides of the midpoint to accommodate removable adjustable-pressure air bladders, foam pads, and/or therapeutic thermal pouches utilizing hot or cold;

(5) the pouches can be positioned medially over the erector spinae muscles or laterally over the lumbodorsal fascia and quadratus lumborum muscles; and (6) the pouches can be filled with a therapeutic pad on one or both sides or remain empty.

For general support or injury prevention purposes, it is advisable to fill and position the pouches in a similar manner to maintain a balanced support over the lower back musculature and spinal structures. However, in certain therapeutic situations where an unbalance in muscular support or spasm exists, the type of therapeutic pad and/or the symmetry of the pouches can be varied between the two sides until the desired therapeutic goal is achieved. Further, adjustment of the support on either or both sides can be achieved by repositioning either of the ends of the elastic member on the ends of the external shell to adjust the tension exerted by the elastic member.

Finally, it should be noted that various other changes and modifications will become apparent to those of ordinary skill in the art reviewing the detailed description above. For instance, the pouches 10 and central region 1 of the external shell may be provided with cooperating fasteners to detachably secure the pouches in the desired position thereof. It is to be understood, therefore, that such changes and modifications may be employed without departing from the spirit of the invention as defined by the scope of the appended claims.

Figure 5:
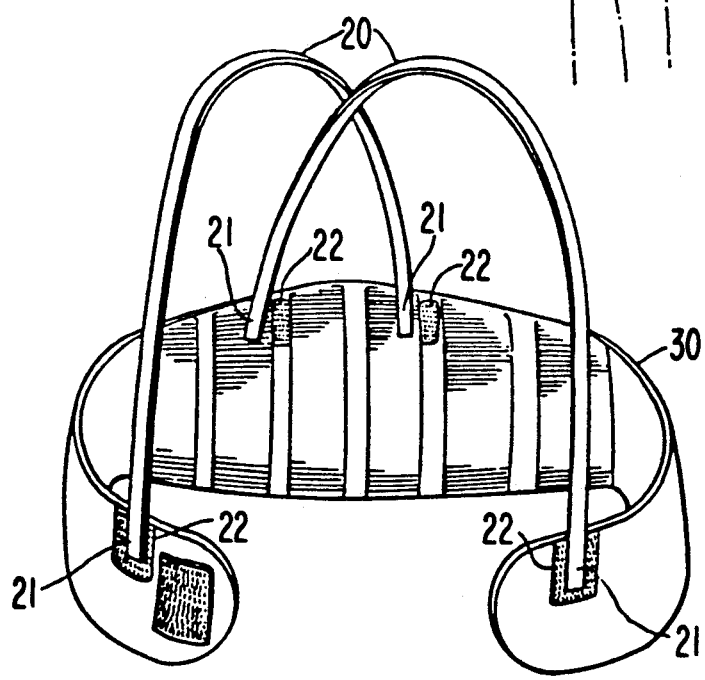
FIG. 5 is a perspective view of the appliance of the present invention including the break away suspenders of a preferred embodiment.

Referring now to FIG. 5, the break away shoulder suspenders of the present invention will be described.

In the preferred embodiment, suspender straps 20 are provided of an elastic woven material. The width and the length of the straps 20 may vary depending on the size of the user and/or the amount of weight which the suspenders are to support. Hook-type fastening members 21 are provided at each end of the straps 20. In the preferred embodiment, the hook-type fastening members 21 face inwardly toward the lumbar support appliance 30 when worn. Affixed to the lumbar support appliance 30 are loop-type fasteners 22. The loop-type fasteners face outwardly from the lumbar support appliance 30 to engage the hook-type fasteners 21 of the straps 20.

The connecting area of each of the loop-type fastening members 22 may be provided in such a size as to permit height adjustment and side-to-side adjustment of the straps 20. For example, the width of each loop type fastening member 22 can be wider than that of each respective hook-type fastener 21. Consequently, the shoulder suspenders can be positioned to maximize comfort and to minimize potential entanglements.

Optionally, the straps of the suspenders may be affixed to each other at a location corresponding to the back and below the shoulder of the user where the straps 20 cross over as shown in FIG. 5.

By the provision of the break away shoulder suspenders of the present invention, it should be clear that the following features and advantages, among others, are obtained:

(1) potential injury to the user resulting from snagging of the suspenders is reduced by the provision of the hook-type and loop-type fastening members;

(2) the loop-type fastening members are provided in such a manner as to permit vertical and side-to-side adjustments of the shoulder suspenders to account for varying sizes of upper torsos of individual users, to maximize overall comfort and to minimize potential entanglements;

(3) the lumbar support device can be loosened to permit evaporation of moisture and dissipation of heat while conveniently allowing the user to position and/or store the support device on the user; and (4) in the event that the shoulder suspenders are not desired, the shoulder suspenders can be simply detached from the body of the lumbar support device.

What is claimed is:

1. A therapeutic appliance securable in an operative orientation around the abdominal region of the body for use in therapeutically treating the lumbar area and upper portion of the sacrum, said appliance comprising:

an external shell having opposite ends, a length as taken in a longitudinal direction of the appliance between said ends that is sufficient to enable said shell to extend around and encircle the abdominal region of the body, a central region between said ends having a width as taken transversely to said longitudinal direction that is sufficient to enable the central region to cover the lumbar area and upper portion of the sacrum, and closure means at said opposite ends for detachably securing the ends together so as to allow the appliance to be detachably secured around the abdominal region of the body; and pouches each having several sides, each said pouch being attached to said external shell through only one of said sides of the pouch such that each said pouch is pivotable relative to said external shell about the one side through which the pouch is attached to the shell, each said pouch being located at the central region of said shell to a respective side of the midpoint between said opposite ends of the shell, and each said pouch pivotable between a first position at which the pouch is disposed at such a location between said midpoint and a respective one of the ends of said shell as to overlie the lumbodorsal fascia and quadratus lumborum muscles when the shell is secured in the operative orientation of the appliance around the abdominal region of the body and a second position at which the pouch is disposed at such a location closer to said midpoint from said first position as to overlie the erector spinae muscles when the shell is secured in the operative orientation of the appliance around the abdominal region of the body.

2. A therapeutic appliance as claimed in claim 1, and further comprising a band-like elastic member extending over the central region of said shell and having opposite ends secured to opposite ends of said shell.

3. A therapeutic appliance as claimed in claim 2, wherein said shell and said elastic member include fastening means at the ends thereof for allowing the ends of said elastic member to be detachably secured to said shell at various locations along the ends of said shell.

4. A therapeutic appliance as claimed in claim 2, wherein said elastic member includes an upper elastic band extending across said central region at such a location as to be aligned transversely across the lumbar area when the appliance is secured in the operative orientation around the abdominal region, and a lower elastic band inclined upwardly from a central section thereof toward said upper elastic band.

5. A therapeutic appliance as claimed in claim 3, wherein said elastic member includes an upper elastic band extending across said central region at such a location as to be aligned transversely across the lumbar area when the appliance is secured in the operative orientation around the abdominal region, and a lower elastic band inclined upwardly from a central section thereof toward said upper elastic band.

6. A therapeutic appliance as claimed in claim 3, wherein said fastening means are hook and loop type of fasteners.

7. A therapeutic appliance as claimed in claim 1, and further comprising foam pads disposed in said pouches.

8. A therapeutic appliance as claimed in claim 1, and further comprising inflatable air bladders disposed in said pouches.

9. A therapeutic appliance as claimed in claim 1, and further comprising heat-retaining means disposed in said pouches for radiating therapeutic amounts of heat to the lumbar region.

10. A therapeutic appliance as claimed in claim 1, and further comprising cold-pack means disposed in said pouches for applying therapeutic amounts of cold to the lumbar region.

11. A therapeutic appliance as claimed in claim 1, and further comprising a kit including a plurality of pads selected from the group consisting of foam pads, inflatable air bladders, heat retaining means for radiating heat, and cold-pack means for applying cold, each of the pads of said kit insertable into the pouches attached to said shell.

12. A therapeutic appliance as claimed in claim 1, further comprising:
first fastener members secured to said external shell; and
suspender straps each having opposite first and second ends, each of the opposite first and second ends having a second fastener member for releasably engaging the respective first fastener members secured to the external shell;
wherein said first fastener members are one of hook-type and loop-type fasteners and said second fastener members are the other of hook-type and loop-type fasteners.

13. A therapeutic appliance as recited in claim 12, wherein said suspenders straps are elastic.

14. A therapeutic appliance as recited in claim 12, wherein a fastening area of said first fastener members is wider than that of said second fastener members to permit side-to-side adjustment of said suspender straps.

15. A therapeutic appliance as recited in claim 13, wherein a fastening area of said first fastener members is wider than that of said second fastener members to permit side-to-side adjustment of said suspender straps.

16. A therapeutic appliance as recited in claim 12, wherein said first fastener members are located on an outer surface of said external shell and have loop-type fasteners facing outwardly from said external shell.

17. A therapeutic appliance as recited in claim 14, wherein said first fastener members are located on an outer surface of said external shell and have loop-type fasteners facing outwardly from said external shell.

18. A therapeutic appliance securable in an operative orientation around the abdominal region of the body for use in therapeutically treating the lumbar area and upper portion of the sacrum, said appliance comprising:
an external shell having opposite ends, a length as taken in a longitudinal direction of the appliance between said ends that is sufficient to enable said shell to extend around and encircle the abdominal region of the body, a central region between said ends having a width as taken transversely to said longitudinal direction that is sufficient to enable the central region to cover the lumbar area and upper portion of the sacrum, and closure means at said opposite ends for detachably securing the ends together so as to allow the appliance to be detachably secured around the abdominal region of the body;
pouches repositionably attached to said external shell so as to each be movable to a first position at which the pouch is disposed at such a location between said midpoint and a respective one of the ends of said shell as to overlie the lumbodorsal fascia and quadratus lumborum muscles when the shell is secured in the operative orientation of the appliance around the abdominal region of the body and a second position at which the pouch is disposed at such a location closer to said midpoint from said first position as to overlie the erector spinae muscles when the shell is secured in the operative orientation of the appliance around the abdominal region of the body; and
a band-like elastic member extending over said pouches at said one side of the shell and having opposite ends secured to the opposite ends of said shell.

19. A therapeutic appliance as claimed in claim 18, wherein said shell and said elastic member include fastening means at the ends thereof for allowing the ends of said elastic member to be detachably secured to said shell at various locations along the ends of said shell.

20. A therapeutic appliance as claimed in claim 18, wherein said elastic member includes an upper elastic band extending across said central region at such a location as to be aligned transversely across the lumbar area when the appliance is secured in the operative orientation around the abdominal region, and a lower elastic band inclined upwardly from a central section thereof toward said upper elastic band.

21. A therapeutic appliance as claimed in claim 19, wherein said elastic member includes an upper elastic band extending across said central region at such a location as to be aligned transversely across the lumbar area when the appliance is secured in the operative orientation around the abdominal region, and a lower elastic band inclined upwardly from a central section thereof toward said upper elastic band.

22. A therapeutic appliance as claimed in claim 19, wherein said fastening means are hook and loop type of fasteners.

23. A therapeutic appliance as claimed in claim 18, and further comprising foam pads disposed in said pouches.

24. A therapeutic appliance as claimed in claim 18, and further comprising inflatable air bladders disposed in said pouches.

25. A therapeutic appliance as claimed in claim 18, and further comprising heat-retaining means disposed in said pouches for radiating therapeutic amounts of heat to the lumbar region.

26. A therapeutic appliance as claimed in claim 18, and further comprising cold-pack means disposed in said pouches for applying therapeutic amounts of cold to the lumbar region.

27. A therapeutic appliance as claimed in claim 18, and further comprising a kit including a plurality of pads selected from the group consisting of foam pads, inflatable air bladders, heat retaining means for radiating heat, and cold-pack means for applying cold, each of the pads of said kit insertable into the pouches repositionably attached to said shell.

28. A therapeutic appliance as claimed in claim 18, further comprising:
   first fastener members secured to said external shell; and
   suspender straps each having opposite first and second ends, each of the opposite first and second ends having a second fastener member for releasably engaging the respective first fastener members secured to the external shell;
   wherein said first fastener members are one of hook-type and loop-type fasteners and said second fastener members are the other of hook-type and loop-type fasteners.

29. A therapeutic appliance as recited in claim 28, wherein said suspenders straps are elastic.

30. A therapeutic appliance as recited in claim 28, wherein a fastening area of said first fastener members is wider than that of said second fastener members to permit side-to-side adjustment of said suspender straps.

31. A therapeutic appliance as recited in claim 29, wherein a fastening area of said first fastener members is wider than that of said second fastener members to permit side-to-side adjustment of said suspender straps.

32. A therapeutic appliance as recited in claim 28, wherein said first fastener members are located on an outer surface of said external shell and have loop-type fasteners facing outwardly from said external shell.

33. A therapeutic appliance as recited in claim 30, wherein said first fastener members are located on an outer surface of said external shell and have loop-type fasteners facing outwardly from said external shell.

* * * * *